(12) United States Patent
Brooks et al.

(10) Patent No.: US 11,798,663 B2
(45) Date of Patent: Oct. 24, 2023

(54) MAINTAINING CONTEXT OF CLINICALLY RELEVANT INFORMATION WHEN DISPLAYED

(71) Applicant: CERNER INNOVATION, INC., Kansas City, KS (US)

(72) Inventors: Marissa Brooks, Washington, DC (US); Jody Butts, Kansas City, MO (US); Hannah Fiechtner, Kansas City, MO (US); Jean D. Tyler, Leawood, KS (US); Jeff Wall, Overland Park, KS (US)

(73) Assignee: CERNER INNOVATION, INC., Kansas City, MO (US)

( * ) Notice: Subject to any disclaimer, the term of this patent is extended or adjusted under 35 U.S.C. 154(b) by 433 days.

(21) Appl. No.: 16/455,127

(22) Filed: Jun. 27, 2019

(65) Prior Publication Data

US 2020/0005911 A1    Jan. 2, 2020

Related U.S. Application Data

(60) Provisional application No. 62/690,785, filed on Jun. 27, 2018.

(51) Int. Cl.
*G16H 10/60*    (2018.01)
*G16H 50/20*    (2018.01)
(Continued)

(52) U.S. Cl.
CPC .......... *G16H 10/60* (2018.01); *G06F 16/338* (2019.01); *G06F 16/345* (2019.01); *G16H 15/00* (2018.01); *G16H 50/20* (2018.01); *G16H 50/50* (2018.01)

(58) Field of Classification Search
CPC ........ G16H 10/60; G16H 50/20; G16H 15/00; G16H 50/50; G06F 16/338; G06F 16/345;
(Continued)

(56) References Cited

U.S. PATENT DOCUMENTS

| 7,757,183 B2 | 7/2010 | Rutledge et al. |
| 8,332,767 B1 | 12/2012 | Beil et al. |

(Continued)

OTHER PUBLICATIONS

Rind, Visual Exploration of Time-Oriented Patient Data for Chronic Diseases: Design Study and Evaluation, 2011, In: Holzinger, A., Simonic, KM. (eds) Information Quality in e-Health. USAB, Lecture Notes in Computer Science, vol. 7058. Springer, Berlin, Heidelberg (Year: 2011).*

(Continued)

*Primary Examiner* — Joshua B Blanchette
*Assistant Examiner* — Tran N Nguyen
(74) *Attorney, Agent, or Firm* — KRAGULJAC LAW GROUP, LLC

(57) ABSTRACT

Systems, methods, and GUIs are provided for visually communicating clinically relevant information in a manner that maintains context and trends across various sizes of user interfaces, such as smaller user interfaces on mobile devices. In an embodiment, a user interface may display a first timeline area with a first indication of a timespan that represents a portion of the timeline. The first indication of the timespan may be scrollable to change the portion of the timeline displayed. The first timeline area may further comprise a set of clinical diagnoses with corresponding duration indicators. The user interface may also display a second timeline area with a second indication of a timespan, which may mirror the first indication of the timespan. The second timeline area may further comprise a set of diagnostic parameters and associated measurements. The user inter- (Continued)

face may also present a medication area having lists of medications separated by classification.

20 Claims, 9 Drawing Sheets

(51) Int. Cl.
  *G06F 16/338* (2019.01)
  *G06F 16/34* (2019.01)
  *G16H 50/50* (2018.01)
  *G16H 15/00* (2018.01)
(58) Field of Classification Search
  CPC ............ G06F 16/287; G06Q 10/06311; G06Q 10/063114–063118; G06Q 10/06312–06316
  USPC .......................................................... 705/2–3
  See application file for complete search history.

(56) References Cited

U.S. PATENT DOCUMENTS

| | | | |
|---|---|---|---|
| 11,133,094 | B2 | 9/2021 | Tucker et al. |
| 2001/0049673 | A1* | 12/2001 | Dulong ................. G16H 20/10 |
| 2003/0038831 | A1* | 2/2003 | Engelfriet ............ G06Q 10/109 |
| | | | 715/719 |
| 2005/0149361 | A1 | 7/2005 | Saus et al. |
| 2007/0073559 | A1 | 3/2007 | Stangel |
| 2008/0177537 | A1 | 7/2008 | Ash et al. |
| 2009/0254370 | A1 | 10/2009 | Kondo et al. |
| 2010/0010387 | A1* | 1/2010 | Skelton .............. A61N 1/36132 |
| | | | 600/595 |
| 2010/0010586 | A1* | 1/2010 | Skelton .............. A61N 1/36132 |
| | | | 607/62 |
| 2010/0131293 | A1* | 5/2010 | Linthicum ............. G16H 10/60 |
| | | | 715/838 |
| 2011/0172564 | A1* | 7/2011 | Drew ..................... A61B 5/061 |
| | | | 600/587 |
| 2011/0184753 | A1 | 7/2011 | Tripoli |
| 2012/0131507 | A1* | 5/2012 | Sparandara ............ G16H 10/60 |
| | | | 715/833 |
| 2012/0304121 | A1 | 11/2012 | Cahill et al. |
| 2012/0331378 | A1 | 12/2012 | Baioura |
| 2013/0024206 | A1 | 1/2013 | Hughes et al. |
| 2013/0085403 | A1* | 4/2013 | Gunderson ............ A61B 5/363 |
| | | | 600/510 |
| 2013/0163956 | A1* | 6/2013 | Medhurst ........... H04N 21/8547 |
| | | | 386/E5.003 |
| 2014/0068489 | A1 | 3/2014 | Wyland et al. |
| 2014/0330581 | A1 | 11/2014 | Billings et al. |
| 2015/0205937 | A1* | 7/2015 | Hazeltine ........... G09B 19/0092 |
| | | | 434/236 |
| 2016/0077689 | A1 | 3/2016 | Audet |
| 2016/0321399 | A1* | 11/2016 | Ramachandran ....... G16Z 99/00 |
| 2017/0068780 | A1 | 3/2017 | Dobrean |
| 2018/0095938 | A1 | 4/2018 | Monte |
| 2019/0034591 | A1 | 1/2019 | Mossin et al. |
| 2019/0304605 | A1* | 10/2019 | Al-Ali ................. A61B 5/7275 |

OTHER PUBLICATIONS

Non-Final Office Action received for U.S. Appl. No. 16/731,734, dated Nov. 13, 2020, 12 pages.
Final Office Action received for U.S. Appl. No. 16/731,734, dated Mar. 24, 2021, 12 pages.
Non-Final Office Action received for U.S. Appl. No. 16/455,129, dated Sep. 3, 2021, 20 pages.
Final Office Action received for U.S. Appl. No. 16/455,129, dated Mar. 24, 2022, 23 pages.
U.S. Patent and Trademark Office, Non-Final Office Action issued in U.S. Appl. No. 16/455,129, filed Jun. 27, 2019, dated Dec. 16, 2022 (26 pgs).
U.S. Patent and Trademark Office, Notice of Allowance issued in U.S. Patent Application No. 16/455, 129 (filed Jun. 27, 2019), dated Jul. 19, 2023 (15 pgs).

* cited by examiner

MAINTAINING CONTEXT OF CLINICALLY RELEVANT INFORMATION WHEN DISPLAYED

CROSS-REFERENCE TO RELATED APPLICATIONS

This application, filed on Jun. 27, 2019, entitled Maintaining Context of Clinically Relevant Information When Displayed, claims the benefit of priority to U.S. Provisional Patent Application No. 62/690,785, filed on Jun. 27, 2018, entitled Maintaining Context of Clinically Relevant Information When Displayed, which is hereby incorporated by reference in its entirety.

TECHNICAL FIELD

Aspects of the technology described herein relate to maintaining context of clinically relevant data across various user interfaces.

BACKGROUND

As is well known, over the last two decades, the use of electronic health record technology has rapidly increased. Hospitals and other healthcare entities rapidly adopted the emerging electronic health record systems because of the advantages they provide over conventional paper-based systems. Moreover, the U.S. Congress spurred the rapid adoption of electronic health record systems by mandating many healthcare entities to switch from conventional paper-based systems to electronic health record systems.

This adoption, however, did not come without challenges. Early electronic systems came with many of the disadvantages and problems that the paper-based systems faced. For example, paper-based systems resulted in patient information being stored at different healthcare facilities. Many times it would be difficult to consolidate this information for a single clinician to review, which is advantageous in making medical decisions. While requests could be made to the various facilities having this information, it would typically require days or weeks to receive it. Once received, much of the information was duplicative. Thus, paper-based systems often provided a clinician with partial medical records or large duplicative records. Neither were optimal when reviewing to provide care to a patient.

As noted, many early electronic health record systems came with these same problems. Electronic records were stored on different media at different healthcare facilities. While electronic systems more easily shared medical records, problems with large duplicative records still existed. Additionally, problems with partial medical records still existed where a patient was not able to inform a treating clinician with information necessary to collect the patient's medical records, such as if the patient came into an emergency department unconscious. Again, this provides problems when clinicians try to review the patient information to determine the best treatment.

As a result, efforts have been made to provide ways for physicians to quickly and easily review historical patient information in an efficient and rapid manner. However, many of these efforts have failed due to limitations in the technology. One limitation that has progressively presented a problem is the decreasing size of user interfaces. Early efforts to efficiently provide information for review did not account for smaller user interfaces, such as those found on today's smartphones. Conventional ways to efficiently provide information did not always conform to these smaller interfaces.

To try to overcome these problems, initial efforts included "shrink-to-fit" designs, in which case the information displayed on larger screens would be reduced to the size of the smaller displays. However, due to large amounts of information displayed, this method was limited because smaller mobile-type user interfaces would provide the information in a manner that was not readable to the clinician, and created input problems because the input areas were too small. Other methods included limiting information or compartmentalizing information. The former created problems for clinicians who needed more information to make decisions, resulting in the clinician reverting back to a larger interface. The latter attempted solution required navigating large numbers of links to view all of the clinically relevant medical information, which may result in missing certain information and could not show trends among patient data.

SUMMARY

This summary is intended to introduce a selection of concepts in a simplified form that are further described below in the detailed description section of this disclosure. This summary is not intended to identify key or essential features of the claimed subject matter, nor is it intended to be used as an aid in determining the scope of the claimed subject matter.

At a high level, aspects described herein relate to systems and methods for presenting clinically relevant information in a manner than can be utilized across various sized user interfaces, including those found in mobile devices, while continuing to maintain context and show trends among the patient information. In some cases, the technology may be provided as a workflow or as part of a workflow. In some cases, the technology provides an overview of relevant clinical data in a flowsheet that allows for correlation of clinical events, aids in reviewing and assessing patient conditions, and helps determine treatments. In some cases, the technology may be presented as a timeline that displays client-defined, e.g., pre-configurable or selectively configured, elements that assist in efficient management of a patient by a clinician.

In some cases, the technology may be provided as a configurable, custom timeline view that displays therapeutic drug classes and client-defined clinical results that are unique to the specific body system or condition. In some cases, information may be presented in the form of ongoing problems or resolved problems, which in some cases may be determined by diagnosis codes in a health record. In some cases, additional information about ongoing and/or resolved problems may be accessed via an input, such as a cursor hover, that initiates a pop-up display. In some cases, medications and medication information may be displayed and grouped by classification, such as drug classification or therapeutic classification.

In an aspect, a first timeline area is presented. The first timeline area may have a first indication of a timespan that presents all of or a portion of a determined timeline. The determined timeline may include relevant dates associated with particular events. The first indication of the timespan may provide these dates equidistant to save horizontal space. The first timeline area may also comprise a set of clinical diagnoses that have a duration indicator, which is expanded or compressed based on the dates in the first indication of the timespan.

In an aspect, a second timeline area is presented. The second timeline area may have a second indication of the timespan, which mirrors the first indication in some cases. The second timeline area may further include a set of diagnostic parameters with measured values that are associated with the dates on the timeline. In an aspect, a medication area is presented. In some cases, the medication area may present lists of patient medication groups by classification and separated by tabs to save vertical space.

In another aspect, a method of generating and presenting a graphical user interface (GUI) having clinically relevant data is provided. The method may receive patient information, and extract and store usable information from the received raw information. A timeline may be determined based on the extracted information. The GUI may be generated and presented based on the timeline, while providing information corresponding to the timeline, such as information related to clinical diagnoses, measured values for diagnostic parameters, and patient medication.

Accordingly, one aspect provides a system for configuring clinically relevant data to maintain trend context when displayed on a user interface. The system comprises: at least one processor; the user interface in communication with the at least one processor; and one or more computer-readable storage devices storing instructions that, when executed by the at least one processor, cause the user interface to present: a first timeline area, the first timeline area comprising: a first indication of a timespan presented horizontally between a first boundary and a second boundary, wherein the first indication of the timespan represents at least a portion of a generated timeline, a set of clinical diagnoses presented vertically, and a duration indicator associated with a clinical diagnosis of the set of clinical diagnoses, the duration indicator having an onset date end associated with an onset date of the clinical diagnosis and a duration region beginning at the onset date end and extending horizontally therefrom, wherein the duration region is expanded and compressed based on the first indication of the timespan.

Another aspect provides for one or more computer-readable storage devices storing instructions that, when executed a processor, cause a user interface to present: a first timeline area, the first timeline area comprising: a first indication of a timespan presented horizontally between a first boundary and a second boundary, wherein the first indication of the timespan represents at least a portion of a generated timeline, a set of clinical diagnoses presented vertically, and a duration indicator associated with a clinical diagnosis of the set of clinical diagnoses, the duration indicator having an onset date end associated with an onset date of the clinical diagnosis and a duration region beginning at the onset date end and extending horizontally therefrom, wherein the duration region is expanded and compressed based on the first indication of the timespan.

Yet another aspect provides for one or more computer-readable storage devices storing instructions that, when executed a processor, cause a user interface to present: a first timeline area comprising: a first indication of a timespan presented horizontally, a set of clinical diagnoses presented vertically, and a duration indicator associated with a clinical diagnosis of the set of clinical diagnoses, the duration indicator having an onset date end associated with an onset date of the clinical diagnosis and a duration region beginning at the onset date end and extending horizontally therefrom, wherein the duration region is expanded or compressed based on the first indication of the timespan; and a second timeline area comprising: a second indication of the timespan presented horizontally, and a set of diagnostic parameters presented vertically, wherein diagnostics results corresponding to the set of diagnostic parameters are presented in a grid relative to the second indication of the timespan and the set of diagnostic parameters.

Yet another aspect provides for a method, system, and/or computer-readable storage devices having instructions for receiving historical EHR information for an individual, the EHR information comprising at least a diagnosis event; parsing the historical EHR information to determine a first date associated with the diagnosis event and extracting the diagnosis event and the first date; determining a timeline based on the first date by including the first date on the timeline; generating a first timeline area comprising: a vertical set of clinical diagnoses that includes a clinical diagnosis corresponding to the diagnosis event, a horizontal first indication of a timespan that includes at least a portion of the timeline, and a duration indicator horizontally aligned with the clinical diagnosis, the duration indicator having a first end vertically aligned with the first date and a duration region extending horizontally from the first end; and communicating the first timeline area for visual presentation on a user interface.

Additional objects, advantages, and novel features of the technology will be set forth in part in the description which follows, and in part will become apparent to those skilled in the art upon examination of the following or learned by practice of the technology.

BRIEF DESCRIPTION OF THE DRAWINGS

The present technology is described in detail below with reference to the attached drawing figures, wherein:

FIG. 2 is an example user interface having an embodiment of a display comprising contextually relevant information, in accordance with an aspect described herein;

FIG. 3 is the display of FIG. 2 additionally including an example date pop-up window, in accordance with an aspect described herein;

FIG. 4 is the display of FIG. 2 additionally including an example duration indicator pop-up window, in accordance with an aspect described herein;

FIG. 5 is an example user interface having another embodiment of a display comprising contextually relevant information, in accordance with an aspect described herein;

FIG. 6 is an example user interface having another embodiment of a display comprising contextually relevant information, in accordance with an aspect described herein;

DETAILED DESCRIPTION

The subject matter of the present technology is described with specificity herein to meet statutory requirements. However, the description itself is not intended to limit the scope of this disclosure. Rather, the inventors have contemplated that the claimed or disclosed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

With regard to the drawings in general, we show certain items in block-diagram form more for being able to reference something consistent with the nature of a patent rather than to imply that a certain component is or is not part of a certain device. Similarly, although some items are depicted in the singular form, plural items are contemplated as well (e.g., what is shown as one data store might really be multiple data stores distributed across multiple locations). But showing every variation of each item might obscure some embodiments. Thus for readability, we show and reference items in the singular (while fully contemplating, where applicable, the plural).

Figure 1:
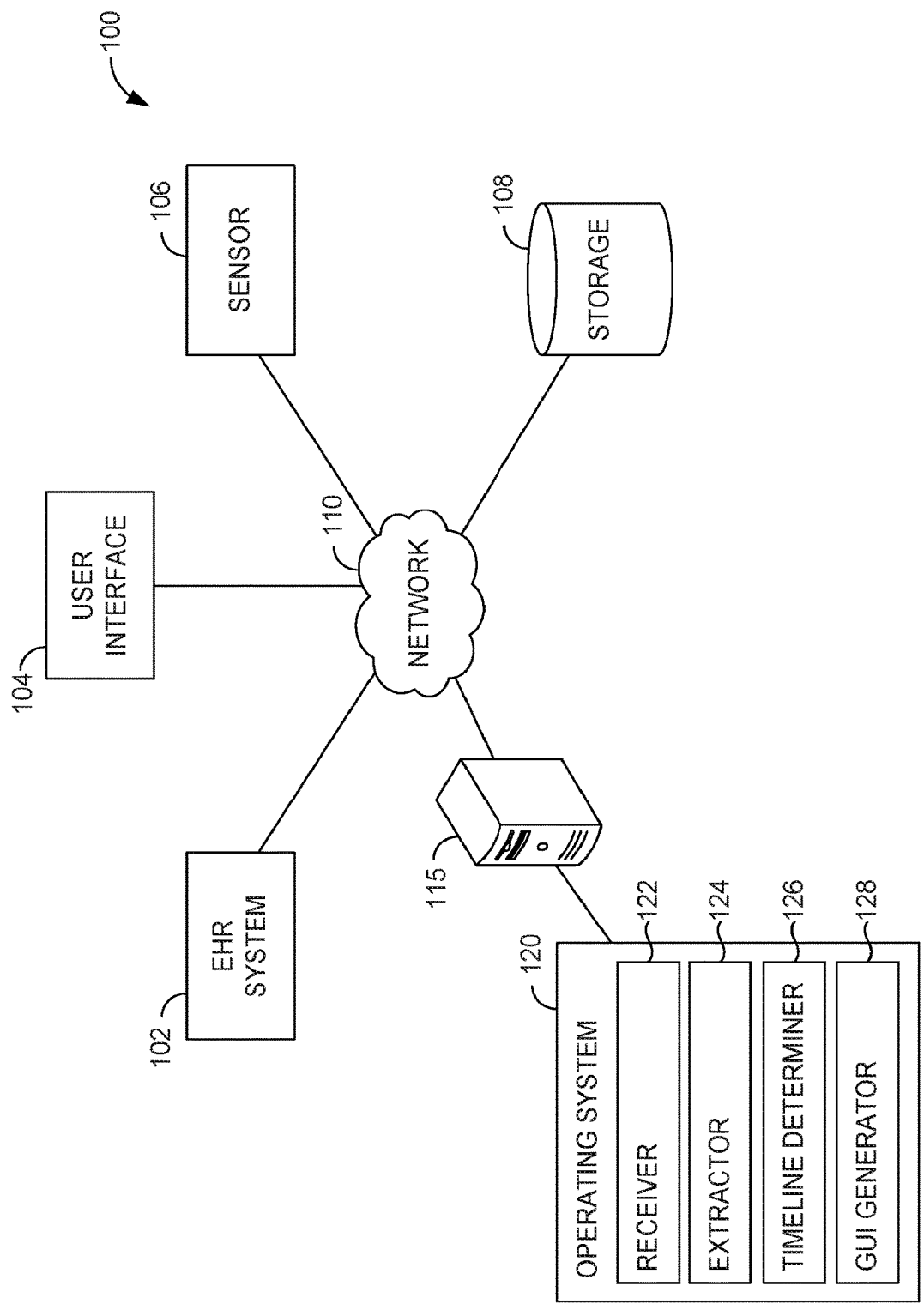
FIG. 1 is an example operating environment suitable for use in practice of the technology, in accordance with an aspect described herein.

Turning now to FIG. 1, an example operating environment 100 for providing visual information that maintains trends and context is illustrated. As illustrated in FIG. 1, the example operating environment 100 includes an electronic health record (EHR) system 102, a user interface 104, a sensor 106, a data storage 108, and a computing device 115. Each of these elements is shown communicating through network 110. Computing device 115 is shown including operating system 120. The operating system 120, as shown in FIG. 1, includes receiver 122, extractor 124, timeline determiner 126, and graphical user interface (GUI) generator 128. Each of these elements will be described in more detail below.

As noted above, each of these components may communicate through network 110. Network 110 may include, without limitation, one or more local area networks (LANs) and/or wide area networks (WANs). In example implementations, network 110 comprises the Internet and/or a cellular network, amongst any of a variety of possible public and/or private networks. Other wireless technologies for transferring data, such as Bluetooth, are contemplated as well. Though components of operating environment 100 are shown communicating through network 110, other arrangements are contemplated. For example, one or more of the components of operating environment 100 may be in direct communication via a communication bus.

It will be understood that the operating environment 100 is provided only as an example of one embodiment suitable for practicing the technology. Other arrangements of elements (e.g., components, machines, interfaces, functions, orders, groupings of functions, etc.) can be used in addition to or instead of those shown, while some may be omitted from FIG. 1 for the sake of clarity in describing the technology.

EHR system 102 may include one or more data stores of health records, which may be included in storage 108, and may further include one or more computers or servers that facilitate the storing and retrieval of the health records. Although storage 108 is depicted as a single data store component, storage 108 may be embodied as one or more data stores or may be in the cloud. In some embodiments, EHR system 102 may be implemented as a cloud-based platform or may be distributed across multiple physical locations and may be the same as or distinct from storage 108. EHR system 102 may further include record systems, which store real-time or near real-time patient (or user) information, such as wearable, bedside, or in-home patient monitors, for example, and may store patient EHRs. For example, EHR systems 160 may comprise one or a plurality of EHR systems such as hospital EHR systems, health information exchange EHR systems, ambulatory clinic EHR systems, or other systems having health-related records for one or more patients, and may be implemented in computing device 115.

Generally, EHRs, sometimes referred to as electronic medical records (EMRs), may comprise electronic clinical documents such as images, clinical notes, orders, summaries, reports, analyses, information received from clinical applications and medical devices, or other types of electronic medical documentation relevant to a particular patient's condition and/or treatment. Electronic clinical documents may contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, clinician assignments, and a host of other relevant clinical information. The content and volume of such information in an EHR system are not intended to limit the scope of the present disclosure in any way.

User interface 104 is also illustrated in operating environment 100. An embodiment of user interface 104 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. Embodiments of user interface 104 may facilitate accessing, receiving, and communicating information from a user or healthcare provider about a specific patient or population of patients, such as patient history; healthcare resource data; variables measurements, time series, and predictions (including plotting or displaying the determined outcome and/or issuing an alert) described herein; or other health-related information, and facilitates the display of results, recommendations, or orders. For example, user interface 104 may communicate with EHR system 102 through network 110 to receive patient EMRs or any other information stored in EHR system 102. In another example, user interface 104 may communicate with sensor 106 to receive any real-time or near real-time patient information.

In some embodiments, user interface 104 may include a GUI for conveying visual information. The user interface 104 may take the form of a computer monitor, which may be in communication with a server to receive information and visually convey it using the GUI. For example, computer monitors may include stand-alone monitors that are independent of the processor and are in communication with the processor through a communication bus or through wireless technology. Such computer monitors may generally be any shape and size. For example, as measured along the diagonal, a computer monitor may be from about 10 inches to about 60 inches, from about 10 inches to about 40 inches, from about 10 inches to about 35 inches, from about 10 inches to about 30 inches, from about 15 inches to about 27 inches, or from about 20 inches to about 25 inches, with "about" meaning plus or minus 10% in this example and throughout this disclosure.

In some embodiments, user interface 104 may be integrated with one or more other computer components, such as storage hardware or processors. For example, such computer systems may include laptops, tablets, smartphones, and the like. These systems may be considered mobile devices. User interfaces associated with mobile devices may be smaller than the computer monitors previously described. For example, mobile device user interfaces may be, as measured along the diagonal, from about 4 inches to about 20 inches, from about 6 inches to about 17 inches, from about 7 inches to about 15 inches, from about 8 inches to about 13 inches, from about 9 inches to about 12 inches, from about 4 inches to about 8 inches, or from about 5 inches to about 7 inches. Some special mobile devices may have user interfaces that are greater than 20 inches, while others may have user interfaces less than 4 inches. These special mobile devices are also contemplated within the scope of and may also be suitable for use with the present technology. Mobile devices may communicate with other technologies, such as other components of FIG. 1, through wireless capabilities, such as using network 110.

In some aspects, user interface 104 may be touch sensitive. In general, a touch sensitive user interface may receive a user input at the user interface. In some cases, the input received will be determined based on the visual information presented by the GUI of the user interface. For example, touch sensitive user interfaces may detect an input based on sensing electrical conductivity of another object, such as a finger or stylus; based on pressure applied to the user interface; or by determining a position of an object and associating its position with a location of the user interface. These types of touch sensitive user interfaces and others are known in the art and will not be described in detail here for the sake of clarity; however, they are contemplated for use in the present technology.

The example operating environment 100 also includes sensor 106. Sensor 106 generally comprises one or more sensor components operable to acquire clinical or physiological information about a patient, such as various types of physiological measurements, physiological variables, or similar clinical information associated with a particular physiological status of a patient, and which may be acquired continuously, periodically, or as one or more time series. In an embodiment, sensor 106 comprises one or more sensors for measuring heart-related physiological data, such as an electrocardiograph, pulse monitor, blood pressure monitor, and the like; one or more sensors for pulmonary related physiological data, such as respiration rate monitor, $O_2$ saturation monitor, and the like; or any other device for measuring real time, or near real time physiological information about a patient.

In an embodiment, one or more sensor components of sensor 106 may comprise a bedside monitor or a user-wearable sensor component, or a sensor component integrated into the patient's environment, such as the home or hospital. Examples of sensor components include a sensor positioned on the body of the patient (e.g., on or near the user's head, attached to the user's clothing, worn around the user's head, neck, leg, etc.); skin-patch sensor; ingestible or sub-dermal sensor; sensor component(s) integrated into the user's living environment (including the bed, pillow, or bathroom); and sensors operable with or through a smart-phone carried by the user, for example. It is also contemplated that the clinical or physiological information about the patient, such as the monitored variables, may be received from human measurements or automatically determined by sensors in proximity to the patient. For example, in one embodiment, a nurse periodically measures a patient's blood pressure and enters the measurement, for example, by using user interface 104.

As illustrated in FIG. 1, the operating environment also includes a computing device 115. Computing device 115 generally comprises one or more processors operable to receive instructions and process them accordingly, and may be embodied as a single computing device or multiple computing devices communicatively coupled to each other. For example, computing device 115 may process computer-usable instructions stored on computer-readable media. In one embodiment, processing actions performed by system 115 are distributed among multiple locations, such as one or more local clients and one or more remote servers, and may be distributed across the other components of example operating environment 100. In an embodiment, system 115 comprises one or more computing devices, such as a server, desktop computer, laptop, or tablet, cloud-computing device or distributed computing architecture, a portable computing device such as a laptop, tablet, ultra-mobile P.C., or a mobile phone. One example computing system suitable for use in practice of the current technology is described in FIG. 7.

With continued reference to FIG. 1, some embodiments of computing device 115 include a computer software stack, which in some embodiments operates in the cloud, as a distributed system on a virtualization layer within computing device 115, and may include operating system 120. Some embodiments of operating system 120 comprise a distributed adaptive agent operating system. Operating system 120 may be implemented as a platform in the cloud, which is capable of hosting a number of services that may run as a local or distributed stack in the cloud, on one or more personal computers or servers such as system 120. For example, as illustrated in FIG. 1, operating system 120 may host receiver 122, extractor 124, timeline determiner 126, and GUI generator 128.

In some cases, services hosted by operating system 120 are associated with one or more virtual assistant applications, services, or routines. For example, such applications, services, or routines may operate on one or more user devices and servers, such as computing device 115, and may be shared or distributed across one or more user devices and servers, one or more other components, or be implemented in the cloud. Moreover, the functions performed, or services carried out by these functions, may be implemented at appropriate abstraction layer(s) such as the operating system layer, application layer, hardware layer, and the like of the computing system(s).

In some cases, the functions and/or the embodiments described herein can be performed, at least in part, by one or more logic components, which may be stored in data storage 108. For example, and without limitation, illustrative types of logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. In general, the logic comprises rules, conditions, associations, classification or prediction models, pattern inference algorithms, or other criteria utilized by operating system 120 to execute services. In some embodiments, the logic may utilize pattern recognition, fuzzy logic, neural network, finite-state machine, support vector machine, logistic regression, clustering, or machine learning techniques, similar statistical classification processes, or combinations of these processes.

As previously noted, an embodiment of operating system 120 comprises receiver 122, extractor 124, timeline determiner 126, and GUI generator 128. In general, receiver 122 receives information. In some aspects, receiver 122 receives stored patient information, such as EHRs received from EHR system 102. In some aspects, receiver 122 may receive clinical documents or information as an input, for example, a lab assistant, nurse, or document specialist inputting patient information via an input associated with computing device 115 and/or via user interface 104. For example, patient information may include historical clinical diagnoses, such as depression, hypothyroidism, diabetes, pregnancy, and the like. Other examples of patient information include medications taken by the patient and/or prescribed to the patient. In some aspects, the received medication information may correspond to the historical clinical diagnosis, such as if a particular medication (e.g., citalopram) was prescribed for a particular diagnosis (e.g., depression). More examples of patient information include stored measurements related to various physiological parameters. For example, some physiological parameters include weight, body mass index (BMI), thyroxine (T4), Thyroglobulin (Tg), and thyrotropic hormone (TSH), and the like.

Patient information may also include historical physiological measurements associated with the physiological parameters. For example, a patient may have physiological measurements associated with the T4 parameter. This may include one or more measurements determined at different times. Each of the one or more measurements may be included in a patient EHR and may be associated with a timestamp. In some cases, the time stamp may represent the time that the patient information was stored. In addition to or alternatively, the time stamp may represent the time that the patient information was collected. For example, a patient may have their blood drawn to measure the Free T4 parameter on Jan. 10, 2015. The results of the Free T4 measurement, such as 0.95 ng/dL, may be associated with the time stamp of Jan. 10, 2015. The patient may also have other values for Free T4 stored with the EHR from labs drawn at other times, for example, labs drawn on Aug. 21, 2014, and Dec. 11, 2014, may have also have corresponding measurements for values for Free T4. In a similar manner, other patient information stored in the EHR may also be associated with time stamps. For example, medication information may be associated with one or more start dates and end dates, which may also include time stamps for change in dosage or frequency of taking the medication. Another example of patient information having associated time stamps includes clinical diagnoses, which may also include one or more onset dates and termination dates.

In some embodiments, medication may be associated with a therapeutic classification, drug classification, or another form of medication classification. For example, medications may be associated with a therapeutic classification such as pulmonary, diabetes, thyroid, and the like. In some cases, medications may be associated with different drug classifications, such as antibiotics, antidepressants, non-steroidal anti-inflammatories (NSAID). Other systems for classifying medications are known in the art and are contemplated to be within the scope of this disclosure.

While only a few examples of clinical diagnoses, medications, and physiological parameters and/or classifications have been included in this description as examples, it will be recognized that these are only a few of many. Other examples are not included for the sake of brevity, but are intended to be within the scope of this disclosure.

In some embodiments, receiver 122 may also receive real time or near real time patient information, such as measured physiological parameters from sensor 106. As noted above, sensor 106 may measure physiological variables of a patient, such as cardiac or pulmonary variables, which may be received directly by receiver 122 in real time or received by receiver 122 in near real time from a data store associated with the sensor 106, such as storage 108. In some embodiments, receiver 122 may receive patient information and store it temporarily or permanently, such as in storage 108.

Extractor 124 generally parses and extracts information from the raw patient information received by receiver 122, and stores the extracted information in a useable format. For example, raw patient information may be received from and EHR stored on storage 108. Extractor 124 may extract information within the health record such as patient demographics, diagnoses information, medication information, and measured physiological parameter values. Parsing the information may include determining the time stamp associated with each of the entries for the diagnoses, medication information, etc. Parsing may include determining the time stamp information that has been stored in association with an entry, such as a time that a lab test was performed to measure a physiological parameter.

Continuing, parsing the received patient information may include determining date stamps from metadata associated with an entry. For example, a physician may have entered a particular diagnosis (such as by entering an ICD-10 or SNOMED terms) into the patient's EHR. The date the entry was input may be associated as metadata, which when parsed, may be included as on onset date for the diagnosis if one was not expressly input by the physician. Additionally or alternatively, parsing may include determining a therapeutic or drug class for a medication. For example, the medication and its start date may have been input in the EHR with a common medical diagnosis code, such as an ICD-10 code, SNOMED terms, MedDRA entry, etc. Using this information, the therapeutic classification for the drug may be determined and parsed. For example, if a medication was prescribed to treat an ICD-10 code associated with hypothyroidism, the therapeutic class may be determined to be thyroid. Thus, the parsed information may include the medication name, the start date, and the therapeutic classification. In some embodiments, a medication stored in the patient EMR may be cross-referenced with preconfigured stored information relating particular medications to particular therapeutic or drug classifications.

Once parsed, in some embodiments, extractor 124 may store the information in a useable format. For example, clinical diagnoses may be stored with corresponding onset dates and termination dates, while medication information may be stored corresponding to start dates, end dates, drug classifications, or therapy classifications. Historical and real time or near real time values for physiological parameters may be stored with corresponding time stamps. It will be appreciated that patient medical information comprises more than clinical diagnoses, medication information, and physiological parameter measurements. However, for the sake of brevity and to not obscure the disclosure of the present technology, not all patient information can be described. Thus, while certain patient information may not be expressly described herein, it is contemplated by the inventors that receiver 122 may receive any electronically stored or real time patient information, while it is also contemplated that extractor 124 may parse any of the information from receiver 122, extract the parsed information, and temporarily or permanently store the parsed information in a usable format.

Timeline determiner 126 generally uses the information received from or stored by extractor 124 to determine the logical content for visual display. In some embodiments, the timeline determiner 126 determines a timeline of contextually and clinically relevant information. In some embodiments, the timeline may be determined based on a set of clinical diagnoses and relevant dates associated with the set of clinical diagnoses. In general, a "set of clinical diagnoses" may comprise one or more clinical diagnoses. More generally, as used throughout this disclosure, unless otherwise described, a "set" may include one or more data elements, objects, etc.

In an embodiment, the timeline determiner 126 may determine a beginning date and an end date for the timeline. The beginning date may be the first date associated with patient medical information from extractor 124. The end date may be the last date associate with patient medical information from extractor 124. In some aspects, the end date will be the present time and date. In such cases, the end date may continually represent the current time and date. In some aspects, timeline determiner 126 may determine that the beginning date and the end date should be included in the timeline.

In some aspects, timeline determiner 126 may determine that the timeline should include dates associated with ongoing and/or resolved clinical diagnoses. In some aspects, timeline determiner 126 may determine that the timeline should include the relevant dates corresponding to the ongoing and/or resolved clinical diagnoses in chronological order between the beginning date and the end date. For example, clinical diagnoses that have one or more onset dates and not an equal number of termination dates may be considered ongoing clinical diagnoses. For example, a patient may have been diagnosed with hyperlipidemia on Jan. 10, 2015. There may be no indication in the patient information that there has been a termination date associated with the diagnosis. Thus, hyperlipidemia may be considered an ongoing diagnosis. In another example, the patient may have a diagnosis of pregnancy that has an associated termination date based on an electronic entry representing the birth of the child. However, a subsequent pregnancy may have an onset date as of the diagnosis date or an entry estimating a conception date. The subsequent pregnancy may not yet have a termination date associated with the diagnosis, as the patient is still pregnant at the present time, and thus, it may be considered an ongoing diagnosis.

In some aspects, clinical diagnoses with equal number of onset dates and termination dates may be resolved diagnoses. Although resolved, in some cases, the resolved clinical diagnosis may be relevant information. As such, timeline determiner 126 may include the resolved diagnoses and their associated dates on the timeline. The determination whether to include resolved problems and/or ongoing problems in the timeline may be a preconfigured determination. In some cases, the determination to include resolved problems and/or ongoing problems in the timeline may be presented as a selectable option via user interface 104.

In some aspects, the clinical diagnosis may be associated with a diagnostic event. In general, a diagnostic event may be any event related to a diagnosis, a symptom, a treatment, a test, or the like for patient medical condition. The diagnostic event may include an initial diagnosis date, an onset date, a termination date, or the like.

In some aspects, timeline determiner 126 may determine that the timeline should include dates associated with historical or current measurements for diagnostic parameters. In some cases, diagnostic parameters and their associated measurements are considered relevant when they have a clinical relation to a clinical diagnosis. As such, one set of diagnostic parameters will be considered relevant when the timeline includes dates associated with ongoing problems. Another set of diagnostic parameters may be considered relevant when the timeline includes dates associated with both ongoing and resolved clinical diagnoses. Diagnostic parameters may be clinically relevant to a clinical diagnosis if the values associated therewith would aid in diagnosing, controlling, or resolving the clinical diagnosis or another indicated clinical diagnosis. Clinical relevancy of a diagnostic parameter may be determined based on stored or accessed information related to standard of care, insurance guidelines and protocols for certain diagnostic codes, medical and scientific literature, or may be selected as clinically relevant or preconfigured to be clinically relevant to the clinical diagnosis.

In some cases, timeline determiner 126 may include dates associated with all diagnostic parameters measured between the beginning date and the end date. In some cases, the timeline determiner 126 will include dates associated with recently measured diagnostic parameters. What is considered recently measured may be a pre-configurable setting, or in some cases, it may be a selectable option presented by user interface 104. For example, some settings or options for diagnostic parameters that are considered recent may be measurements taken within the last 1 month, 2 months, 3 months, 6 months, 1 year, 2 years, 3 years, 5 years, or any other length of time. In some aspects, timeline determiner 126 may include dates associated with a set of diagnostic parameters that are relevant based on a combination of these factors. For example, timeline determiner 126 may determine that dates should be included in the timeline when the dates are a clinically relevant diagnostic parameter or are recently measured. As an example, hypothyroidism may be an ongoing clinical diagnosis. Timeline determiner 126 may include in the timeline dates associated with values of Free T4, Tg, and Tsh, as they are clinically relevant to hypothyroidism. Timeline determiner 126 may also include dates associated with values for weight and BMI if the values are recently measured, such as values taken within the last 6 months.

In some aspects, timeline determiner 126 may determine that the timeline should include dates associated with historical or current medications taken by the patient. In some cases, timeline determiner 126 may include dates associated with all medications taken by the patient over a preconfigured or selected timeframe, such as within the last 1 month, 2 months, 3 months, 6 months, 1 year, 2 years, 3 years, 5 years, or any other length of time. In addition to or alternatively, timeline determiner 126 may include dates associated with clinically relevant medications. Clinically relevant medications may be those medications associated with ongoing and/or resolved diagnosis. For example, if the patient has an ongoing diagnosis of hypothyroidism, a clinically relevant medication may include levothyroxine. Medication may be determined to be clinically relevant based on stored or access information described previously, for example. In some aspects, timeline determiner 126 may include dates associated with all historical or current medications taken by the patient. For example, these dates may be dates on which the patient took medications, dates on which the patient began or ended a medication regimen, dates on which the patient changed dosage or frequency of taking the medication, and the like. For dates associated with both the set of diagnostic parameters and medications, in some cases, timeline determiner 126 may include the dates in chronological order between the beginning date and the end date of the timeline.

As noted, in some aspects, the timeline determiner 126 determines the timeline by including relevant dates in chronological order. For example, by including the relevant dates, the timeline determiner 126 determines a timeline that is, in some cases, an optimum timeline for presentation in a horizontal direction. This is because, and as will be further described, when the dates are presented equidistant from one another, significantly less horizontal area is required to present the timeline as compared to a "to-scale" timeline. Thus, the timeline determined by timeline determiner 126 is better suited for display on smaller user interfaces where horizontal space is limited.

The GUI generator 128 generally determines how to visually present the timeline and data associated with events on the timeline in a manner than maintains context across various user interfaces, such as monitors and mobile devices, and may communicate the data for display by the user interface. FIGS. 2-5 illustrate various embodiments of visually communicated information on a user interface, such as user interface 104, as generated by GUI generator 128. FIGS. 2-5 will be referenced through the discussion of the GUI generator 128; however, these embodiments are by no means meant the limit the possible visual representations of data that can be generated by GUI generator 128 that still maintain context while providing clinically relevant information, as they are only examples.

Figure 2:
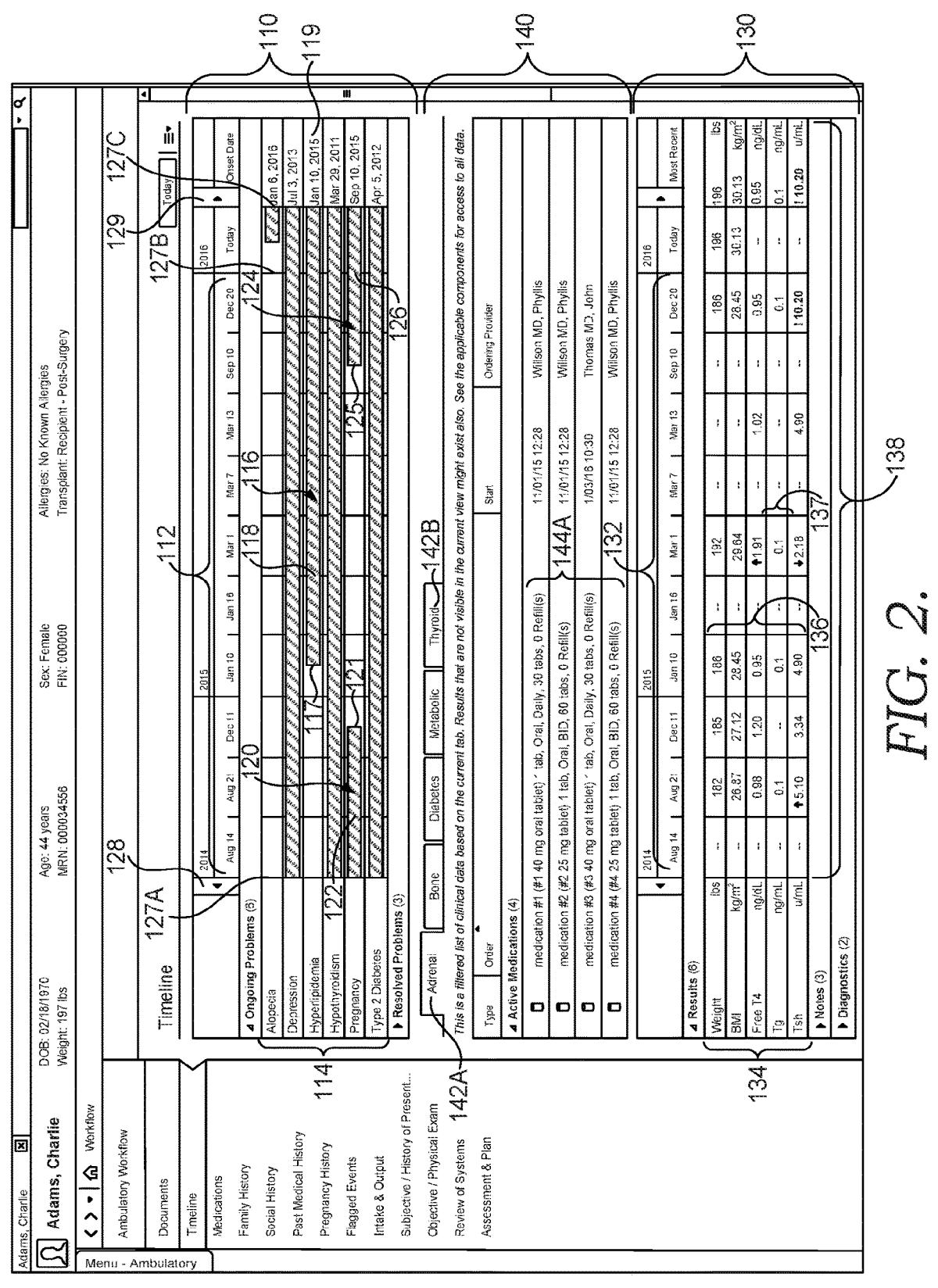

With reference first to FIG. 2, in some embodiments, GUI generator 128 may generate for communication a first timeline area 110. The first timeline area 110 may comprise a first indication of a timespan 112, which in some cases may be presented horizontally. The first indication of the timespan 112 may include all of or a portion of the timeline determined using timeline determiner 126. The first indication of the timespan 112 may comprise the dates that are associated with the timeline. For example, as shown in FIG. 2, the first indication of the timespan 112 comprises dates of Aug. 14, 2014, Aug. 21, 2014, and so forth. In some aspects, the dates included in the timeline may be included in the first indication of the timespan 112 and spaced apart by an equal distance. As an example, Jan. 10, 2015, is shown spaced apart from Jan. 16, 2015, a distance that is equal to the distance between Mar. 13, 2015, and Sep. 10, 2015, although the length of time between these dates varies from about one week to about six months, respectively.

Although FIG. 2 illustrates the first indication of the timespan 112 as having a chronological order that proceeds forward in time from the left to the right, in some cases, the first indication of the timespan 112 may provide for a chronological order that proceeds forward in time from right to left. This embodiment has not been included in the FIGS. for brevity but is contemplated by the inventors to be within the scope of this disclosure.

The first timeline area 110 may also include the set of clinical diagnoses 114. In an embodiment, the first timeline may include an onset date associated with a clinical diagnosis of the set of clinical diagnoses, such as onset date 119. In an embodiment, the set of clinical diagnoses 114 may be presented as a list. In some cases, the list may be presented vertically. GUI generator 128 may present a selectable option for toggling between ongoing diagnoses and resolved diagnoses. In some cases, the option may present both ongoing and resolved diagnoses together as one list or may present them as two separate lists.

As illustrated in FIG. 2, in some aspects, a duration indicator, such as first duration indicator 116 and second duration indicator 120, may be associated with one or more of the clinical diagnoses in the set of clinical diagnoses 114. For example, as illustrated, the first duration indicator 116 is associated with hyperlipidemia, while the second duration indicator 120 is associated with a first pregnancy and the third duration indicator 124 is associated with a second pregnancy. Each of the duration indicators may have an onset date end, a termination date end, and a duration region.

In general, the onset date end may be associated with an onset date of the clinical diagnosis, while the termination date end may be associated with a termination date of the clinical diagnosis. In some cases, the duration region will extend from the onset date end horizontally to the termination date end. In some cases, there is no termination date for the clinical diagnosis, and the duration region may extend from the onset date end to the present date. The duration region may extend horizontally from the onset date end in a direction that is forward in time, which may be left or right relative to the direction of time provided by a timespan indication, such as the first indication of the timespan 112.

In some aspects, the GUI generator 128 expands and contracts a duration region of a duration indicator based on the timespan indication. In some cases, the duration indicator may be expanded over areas of the timespan indication that present shorter lengths of time relative to areas of the timespan indication that present longer lengths of time, in which the GUI generator 128 may contract the duration region. To provide an example, FIG. 2 illustrates the first indication of the timespan 112 having dates that include Jan. 10, 2015; Jan. 16, 2015; Mar. 13, 2015; and Sep. 10, 2015. January 10 and January 16 represent a week in time, while March 13 and September 10 represent six months in time. However, they are respectively spaced apart the same distance in the first indication of the timespan 112. Thus, as an example, GUI generator 128 expands the duration region 118 between January 10 and January 16 while contracting the duration region 118 that is between March 13 and September 10. In some cases, the GUI generator 128 will expand and contract each duration region of each duration indicator in the first timeline area 110. In aspects, expanding and contracting each duration region of the duration indicators allows the GUI to display trends between the various clinical diagnoses over time while reducing the amount of horizontal spaced needed to show these trends. In some cases, this information may be displayed on monitors or mobile device while maintaining the same context of information despite the reduced user interface size of a mobile device relative to a monitor.

In some aspects, the first timeline area 110 may comprise one or more boundaries, such as first boundary 127A, second boundary 127B, and third boundary 127C. In some aspects, the one or more boundaries may define the outer limits of the first indication of the timespan 112 and the associated duration indicators that are displayed at a given time. Put another way, as previously mentioned, the first indication of the timespan 112 may represent only a portion of the timeline determined by the timeline determiner 126. The portion of the timeline that is represented by the first indication of the timespan 112 may be between the one or more boundaries. For example, referencing FIG. 2, the first indication of the timespan 112 may represent only a portion of its associated timeline, which may be defined by boundary 127A and 127B.

In some cases, boundaries may define fixed areas and non-fixed areas. In some case, fixed areas and non-fixed areas may be defined between more than one boundary or between one boundary and another margin, such as the edge of the user interface or the margin of another area or subarea. In general, a fixed area may be an area that remains stationary on the GUI display. The location of fixed areas and the data provided by these fixed areas may be preconfigured and may vary. A non-fixed area is an area that may be manipulated to show different data, different variations, a portion of an overall set of data, or the like and may be manipulated based on a user input. Like fixed areas, the location and data presented by a non-fixed area may be configurable. One example of a non-fixed area is a scrollable area.

FIG. 2 has some examples of fixed areas and non-fixed areas. As illustrated, FIG. 2 shows portions of the first indication of the timespan 112 between three example boundaries 127A-C. Further, as noted previously, the first indication of the timespan 112 may represent only a portion of the timeline determined by timeline extractor 126. Thus, the portion of the first indication of the timespan 112 that is between boundary 127A and boundary 127B may be a non-fixed area. For example, this may be a scrollable area. As such, the portions of the timeline represented by the first indication of the timespan 112 visually presented by the user interface, such as user interface 104, may be manipulated. While other inputs for manipulating this visual representation are contemplated, FIG. 2 shows a past scroll input 128 and a future scroll input 129 that are included in the first timeline area 110. In some embodiments, user inputs (such as touch via a touch-screen user interface or a selection using a cursor) may change the portion of the timeline shown by the first indication of the timespan 112 to show a different portion of the timeline. For example, by selecting the past scroll input 128, the first indication of the timespan 112 may be manipulated to show prior dates and events that are included on the determined timeline but are out of the current view. Similarly, the future scroll input 129 may be selected to show future dates and events included on the determined timeline but are out of the current view. In doing so, the visual information presented in the first indication of the timespan 112 that is between boundary 127A and 127B may appear to scroll left and right.

Other areas of the visual information displayed may be fixed. In some cases, boundaries may be used to define the fixed areas. Looking again to FIG. 2, a portion of the first indication of the timespan 112 between boundary 127B and 127C may be fixed. In this example, as the portion of the first indication of the timespan 112 is manipulated to show different timespans, the area between boundaries 127B and 127C may remain constant. In this example, the fixed area allows a user to continue to see the most present, e.g. "today," relevant information, even while viewing and changing the viewable portions of the timeline represented by the first indication of the timespan 112 between boundaries 127A and 127B.

Thus, in some embodiments, by providing the first indication of the timespan 112 as a scrollable element to manipulate the view of the portion of the determined timeline represented by the first indication of the timespan 112, the horizontal space needed to view the clinically relevant information is reduced. In some cases, this may allow the first timeline area 110 to be presented in the same format or context on larger monitors and smaller mobile devices. In some cases, no different format is needed when viewing the clinically relevant information on a mobile device versus a monitor. Put another way, the first timeline area 110 may look the same on a larger monitor as a small mobile device. While the larger monitor may provide for more of the timeline to be displayed by the timespan indication, such as the first indication of the timespan 112, the same information is easily displayed on a smaller mobile device interface by selecting inputs to scroll through the various portions of the determined timeline. As such, the context of the information is maintained on the small mobile device user interface. This solves a problem in the art whereby different backgrounds and formats are needed for smaller user interfaces to display all of the relevant information. This provides benefits for users because they may only need to be trained on one type of interface, may quickly and easily look up data, and may quickly and easily input data or make decisions because they are familiar with how the information is displayed.

Similarly, maintaining the context of the clinically relevant information between various screen sizes allows for other applications to be utilized with the present technology. Examples include a screen sharing application or a remote desktop application, where the same or similar information is viewed on multiple different interfaces. Instead of shrinking the information to fit a smaller interface, the context is maintained and the information can easily be viewed by simple inputs. This solves another problem in the art of screen sharing or using a remote desktop, whereby viewing on a smaller interface shrinks the information down to a size that may not be legible, thus limiting the types of user interfaces based on size. Similar horizontal space saving displays and methods may be employed to visually represent measured values for diagnostic parameters and to visually represent patient medication information, some examples of which are prescribed below. They may be employed in addition to or in lieu of the first timeline area 110.

In some embodiments, GUI generator 128 may generate a second timeline area 130 having a second indication of a timespan 132. The second timeline area 130 may be presented below the first timeline area 110, such as shown in FIG. 2. In alternative embodiments, the second timeline area 130 may be presented above the first timeline area 110. In an embodiment, the second indication of the timespan 132 is presented horizontally. In some aspects, the second indication of the timespan 132 will be the same as the first indication of the timespan 112. For example, the second indication of the timespan 132 may mirror the first indication of the timespan 112. For instance, if the first indication of the timespan 112 is manipulated to show a particular portion of the generated timeline, the second indication of the timespan 132 may change in response to show the same timespan. In addition to or alternatively, if the second indication of the timespan 132 is manipulated to show a particular portion of the generated timeline, the first indication of the timespan 112 may change in response to show the same timespan.

In some aspects, the second timeline area 130 may comprise a set of diagnostic parameters 134. In some aspects, the diagnostic parameters of the set of diagnostic parameters 134 may be presented as a list. In some aspects, the list of diagnostic parameters may be presented vertically, such as the set of diagnostic parameters 134 in FIG. 2. In some aspects, the second timeline area 130 comprises a grid 138. The grid 138 may be used to represent measurement values (such as diagnostics results 136) for diagnostic parameters taken at certain times, which may be included on the determined timeline and represented by the second indication of the timespan 132. For example, FIG. 2 illustrates a cell 137 having a value of 0.1 ng/mL of Tg that corresponds to Mar. 1, 2015.

In some aspects, by providing values of diagnostic parameter measurements visually corresponding to a date on the timeline, clinically relevant information trends can be detected among the clinically relevant information. This may aid clinicians in diagnosing and treating particular diagnosis. As an example, the portion of the timeline represented by the second indication of the timespan 132 may be the same as the first indication of the timespan 112. Thus, the visual representation of the diagnostic parameter values in the second timeline area 130 may also correspond to the set of clinical diagnoses presented in the first timeline area. Using FIG. 2 as an example, the 0.1 value of Tg measured on Mar. 1, 2015, corresponds to the same Mar. 1, 2015, presented in the first timeline area. Thus, by way of the duration indicators associated with the set of clinical diagnoses, a clinician would quickly recognize that on Mar. 1, 2015, the patient had ongoing diagnoses of depression, hyperlipidemia, hypothyroidism, and type 2 diabetes. In this way, a clinician can quickly and easily detect trends in the patient healthcare data.

In some aspects, GUI generator 128 may generate a medication area 140. In some aspects, the medication area 140 may be presented between the first timeline area 110 and the second timeline area 130, such as in the example shown in FIG. 2. However, it will be understood that the medication area may be located anywhere on the GUI relative to the timeline areas, such as above or below the timeline areas. In some aspects, the medication area 140 may comprise medication information, such as names of medication, dosage, frequency, start date, and the like. In some aspects, the medications and medication information may be presented as a list, such as the list of medications 144A of FIG. 2.

In some cases, GUI generator 128 may present the list of medications 144A in groups. The groups may be based on a classification, such as drug class, therapeutic class, or the like. In some aspects, GUI generator 128 may generate a series of tabs based on the classification of the medications stored in a patient's EHR, where each classification has a tab and the corresponding medications are grouped with each tab based on the medication's classification. For example, if stored patient information indicates that the patient is taking aspirin, ibuprofen, and amoxapine, then two tabs may be generated: NSAID and Antidepressant. Aspirin and ibuprofen may be grouped under NSAID, while amoxapine may be grouped under Antidepressant. In some aspects, only tabs corresponding to stored patient medication information may be generated. Each medication and its associated medication information may be presented upon selection of a tab that corresponds to the medication's classification. In such aspects, selecting tabs by way of a user input allows a user to toggle between various medication lists based on the classification. For example, in FIG. 2, a series of tabs is presented. Each tab, such as tab 142A and 142B, corresponds to a therapeutic class, as the medications in this example are grouped based on their therapeutic classification. As illustrated in FIG. 2, the list of medications 144A corresponds to the adrenal therapeutic classification presented on tab 142A. It will be appreciated that tabs, such as tab 142A and 142B, are configurable, for example by use of a Bedrock tool included for creating timeline views within a system. Thus, for example, tabs may be configured to display specific diseases or diagnoses, such as "diabetes," which could include one or more therapeutic classifications of medications, along with any relevant vitals, labs, clinician notes, and the like associated with the patient's diabetes. In general, tabs maybe configured to include any information that relates to the items displayed when selecting the tab.

Figure 5:
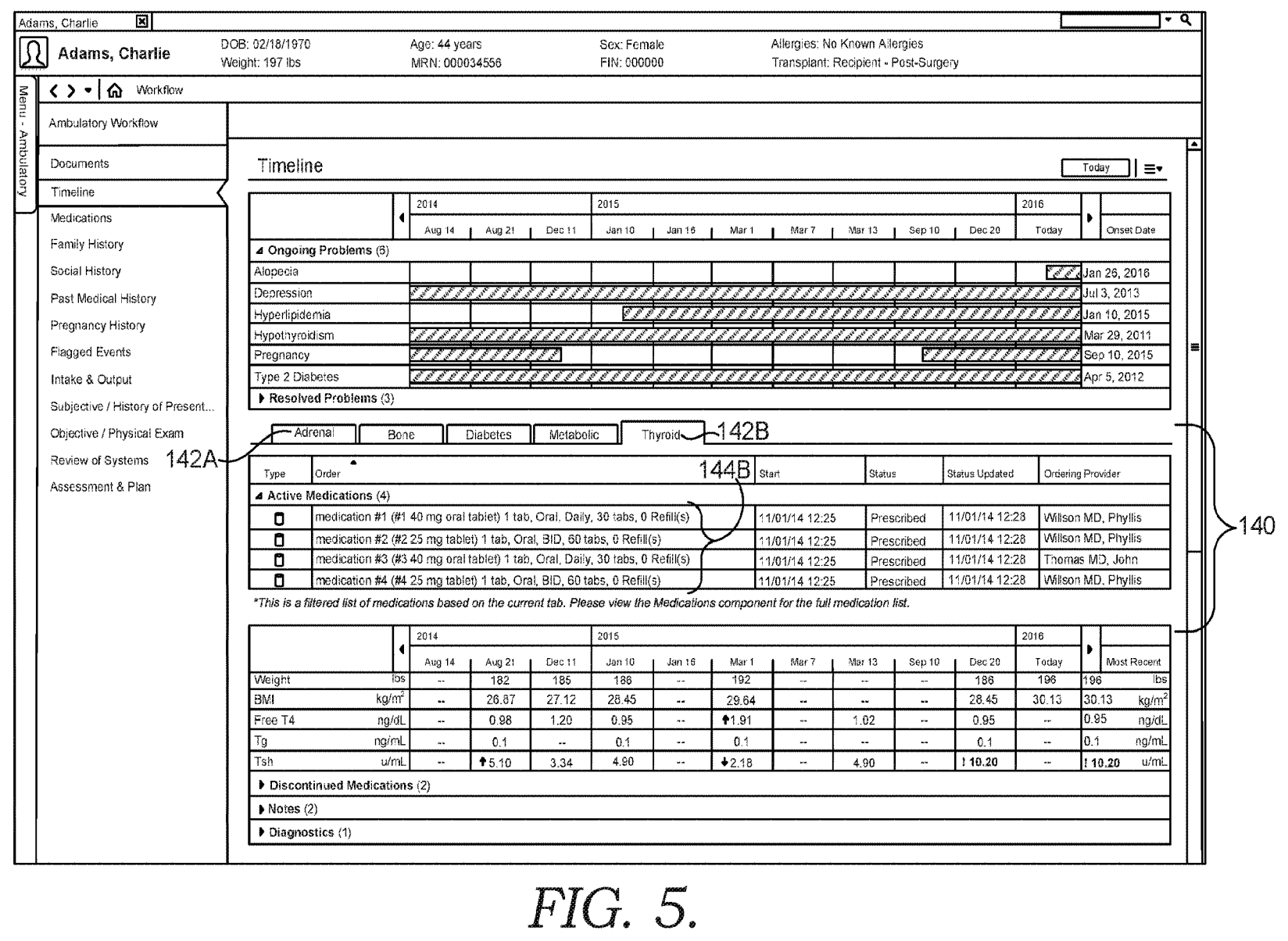

In some cases, a user may change the visual information related to the medications by toggling between various classifications using the series of tabs. As an example, the user may select the thyroid tab 142B to view medications and their associated information related to the thyroid therapeutic classification. By selecting the thyroid tab 142B, the GUI may change to the example shown in FIG. 5. As illustrated in FIG. 5, the list of medications 144B is now presented in the medication area 140. As will be understood, any classification system may be used to generate the various tabs and group the medications accordingly. In some aspects, the classification for grouping the medication information may be preconfigured or provided as a selectable option.

In this manner, by grouping the medications based on a classification, vertical space on the user interface is conserved. For instance, medications provided in a list take up a greater amount of vertical space as the list grows. However, by grouping the medication based on classification, a user can easily toggle between shorter lists of medications, thereby conserving vertical space on the user interface, and the user may not have to exit out of the current display when doing so. As such, in some aspects, the medication area 140 may provide clinically relevant information regarding a patient on smaller user interfaces, such as on mobile devices.

Figure 3:
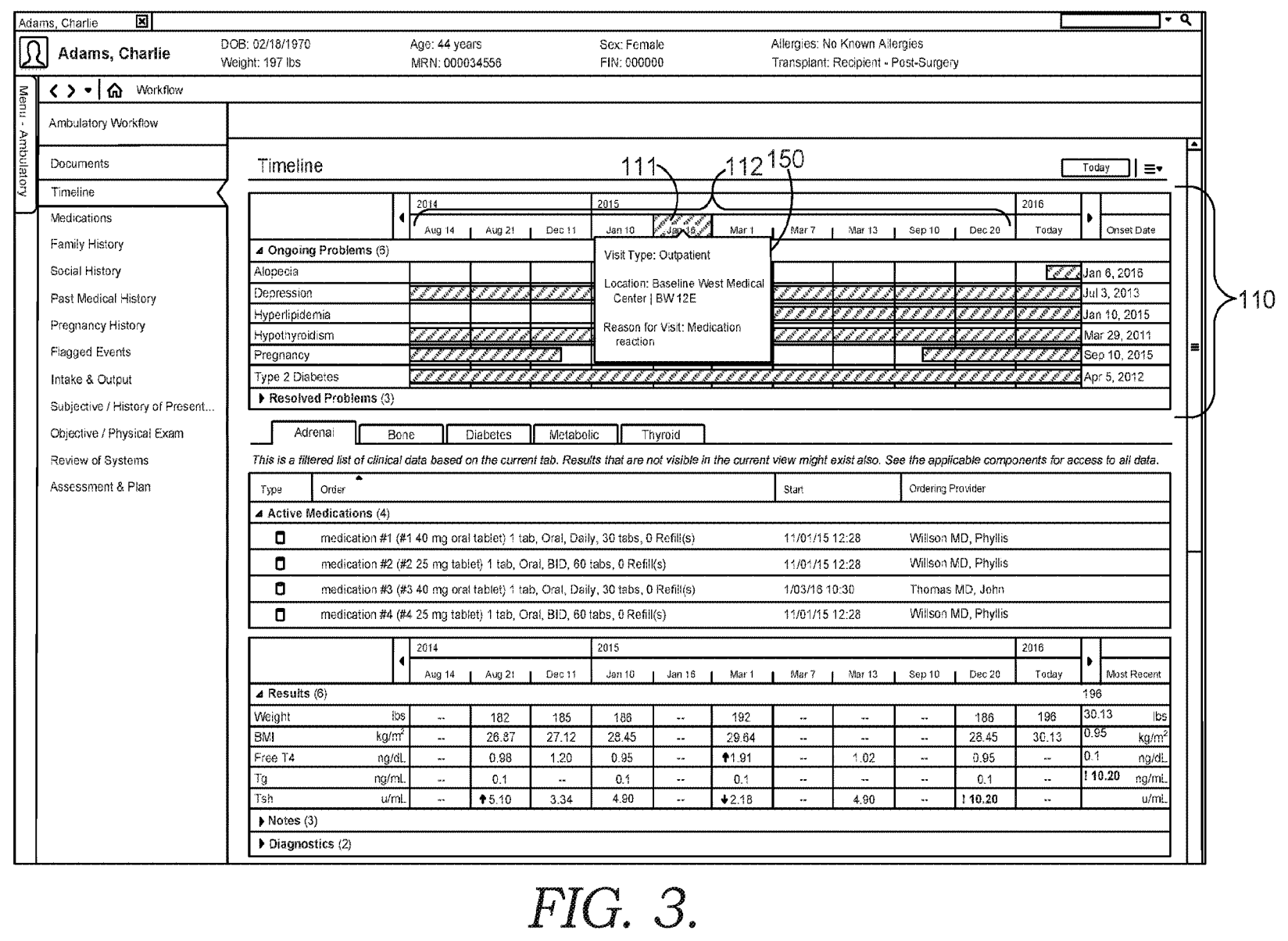

FIG. 3 illustrates another embodiment of the display provided by the GUI generator 128 in FIG. 2. In some embodiments, GUI generator 128 may generate the first indication of the timespan 112 to include one or more dates, such as date 111, which may be included in the timeline determined by timeline determiner 126. GUI generator 128 may generate the dates having metadata links that, in some aspects, are not generally viewable as part of the GUI. The metadata links may provide access to additional information regarding the corresponding date that is tagged. In some aspects, the additional information will not be visible until an input is received at the tagged date. In some aspects, the type of additional information recalled may be preconfigured. Upon receiving the input, the metadata tag may be used to recall the additional information, which will then be displayed in a pop-up window, in some aspects. For example, in FIG. 3, the date 111 has been shaded to indicate that it has received an input. Utilizing the metadata tags linked to the patient EHR and associated with the date 111, the GUI generator 128 recalls additional information about the date 111 stored in the EHR. The additional information is illustrated as being presented in date pop-up window 150.

Figure 4:
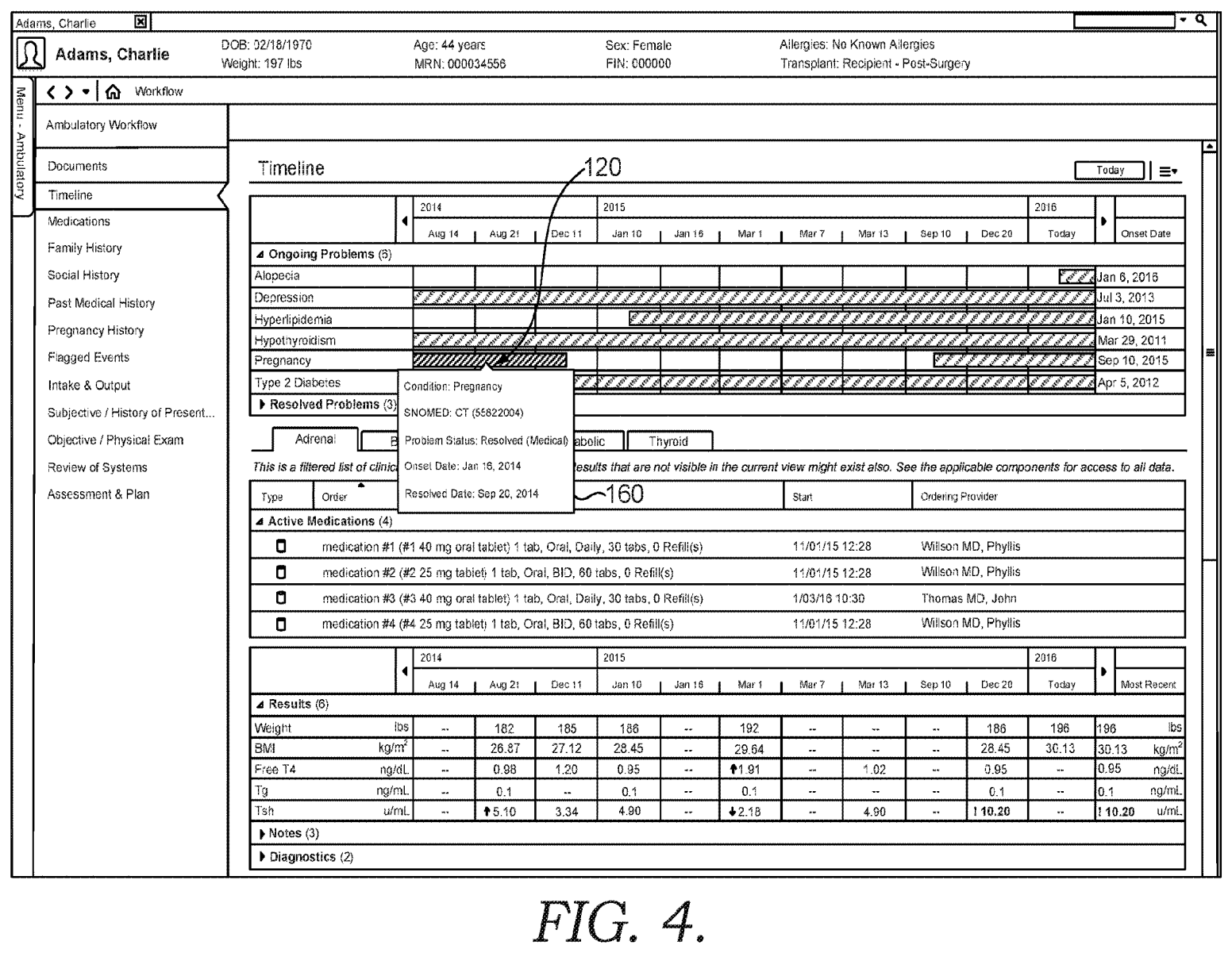

FIG. 4 illustrates another embodiment of the display provided by the GUI generator 128 in FIG. 2. In some embodiments, GUI generator 128 may generate duration indicators, such as the second duration indicator 120, to include metadata links that, in some aspects, are not generally viewable as part of the GUI. The metadata links may provide access to additional information regarding the clinical diagnosis corresponding to the duration indicator. In some aspects, the additional information will not be visible until an input is received at the duration indicator. In some aspects, the additional information recalled may be preconfigured. Upon receiving the input, the metadata tag may be used to recall the additional information, which may then be displayed in a pop-up window. For example, in FIG. 4, the second duration indicator 120 has been shaded darker to indicate that is has received an input. Utilizing the metadata tags linked to the patient EHR and associated with the second duration indicator 120, the GUI generator 128 recalls additional information about the corresponding clinical diagnosis (first pregnancy) that is stored in the EHR. The additional information is illustrated as being presented in duration indicator pop-up window 160.

By including additional information based on using metadata tags and presenting the additional information as a pop-up, additional space in the GUI is conserved. This provides another way that information may be visually communicated to the user in a manner that conserves space and allows for the same format or background to be used across various large and small user interface screen sizes.

Figure 6:
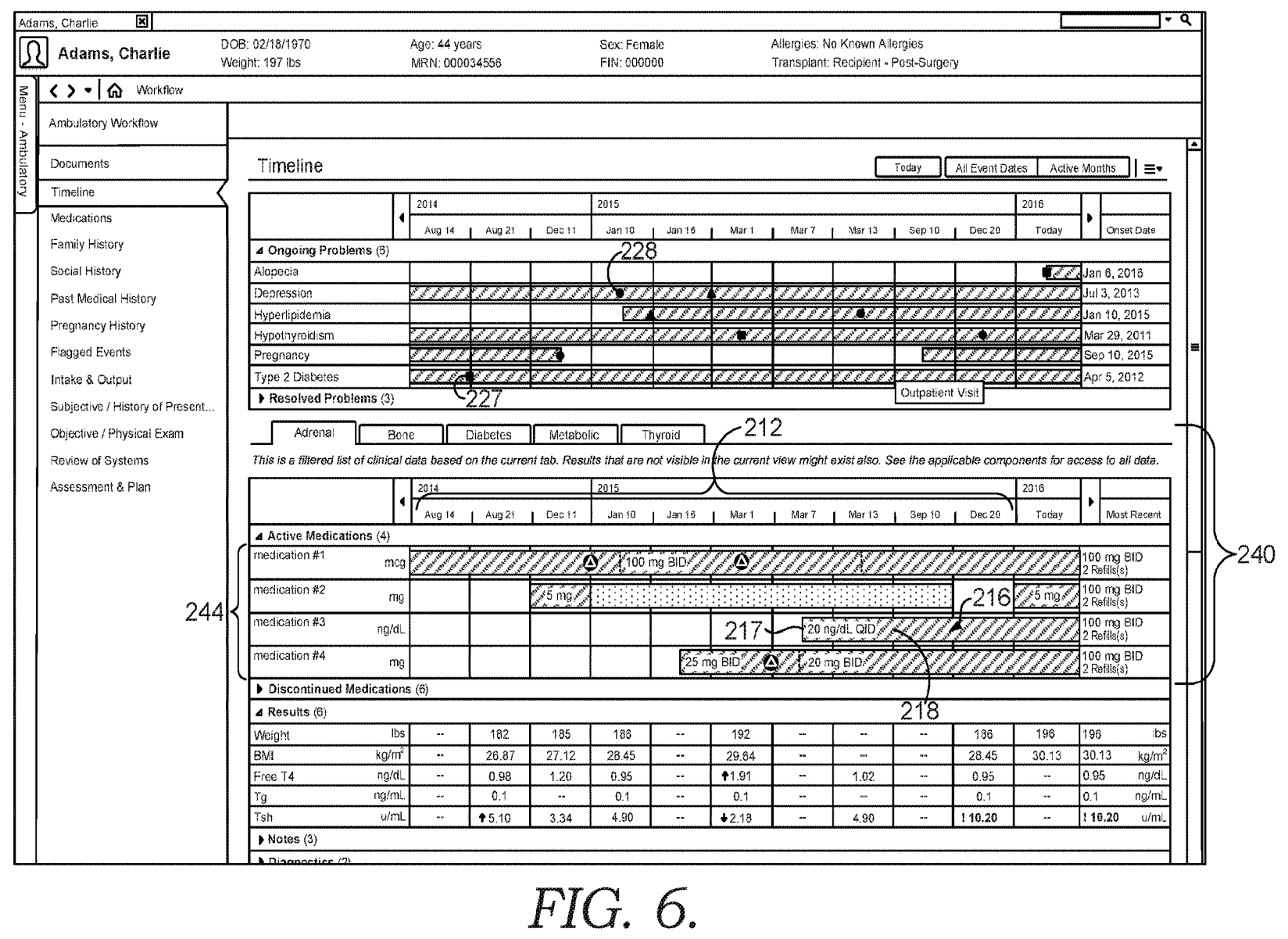

Turning now to FIG. 6, an example user interface having another embodiment of a display comprising contextually relevant information is provided. As illustrated in FIG. 6, medication area 240 comprises a list of medications 244, which in some cases may be group by classification and separated based on the groups, as has been previously described. FIG. 6, illustrates another method of visually conveying medication information associated with the medications, such as using the timeline determined by timeline generator 126.

The medication area 240 may comprise a second indication of a timespan 212. Using methods similar to those previously described, medication area 240 may present medication duration indicators, such as medication duration indicator 216. Medication duration indicators may correspond to a medication. As illustrated, medication duration indicator 216 corresponds to medication #3 under the Adrenal tab. Medication duration indicator 216 may comprise a medication start date illustrated by a medication start end, such as medication start end 217. It may further comprise a duration region, such as duration region 218, that extends from the medication start end.

In some embodiments, metadata tags may be used to reference additional patient information, as has previously been described. In some aspects, data indicators, such as data indicator 227 and 228 may indicate input locations on the GUI for retrieving additional data using the metadata tags. For example an input (e.g., a mouse click or a touch) at one of the data indicators may recall additional information in the patient EHR relative to the location of the data indicator. For example, if the data indicator is on a duration indicator, then the information recalled may correspond to the clinical diagnosis associated with the duration indicator. In some cases, data indicators may be used to represent and recall particular information about particular events.

Figure 7:
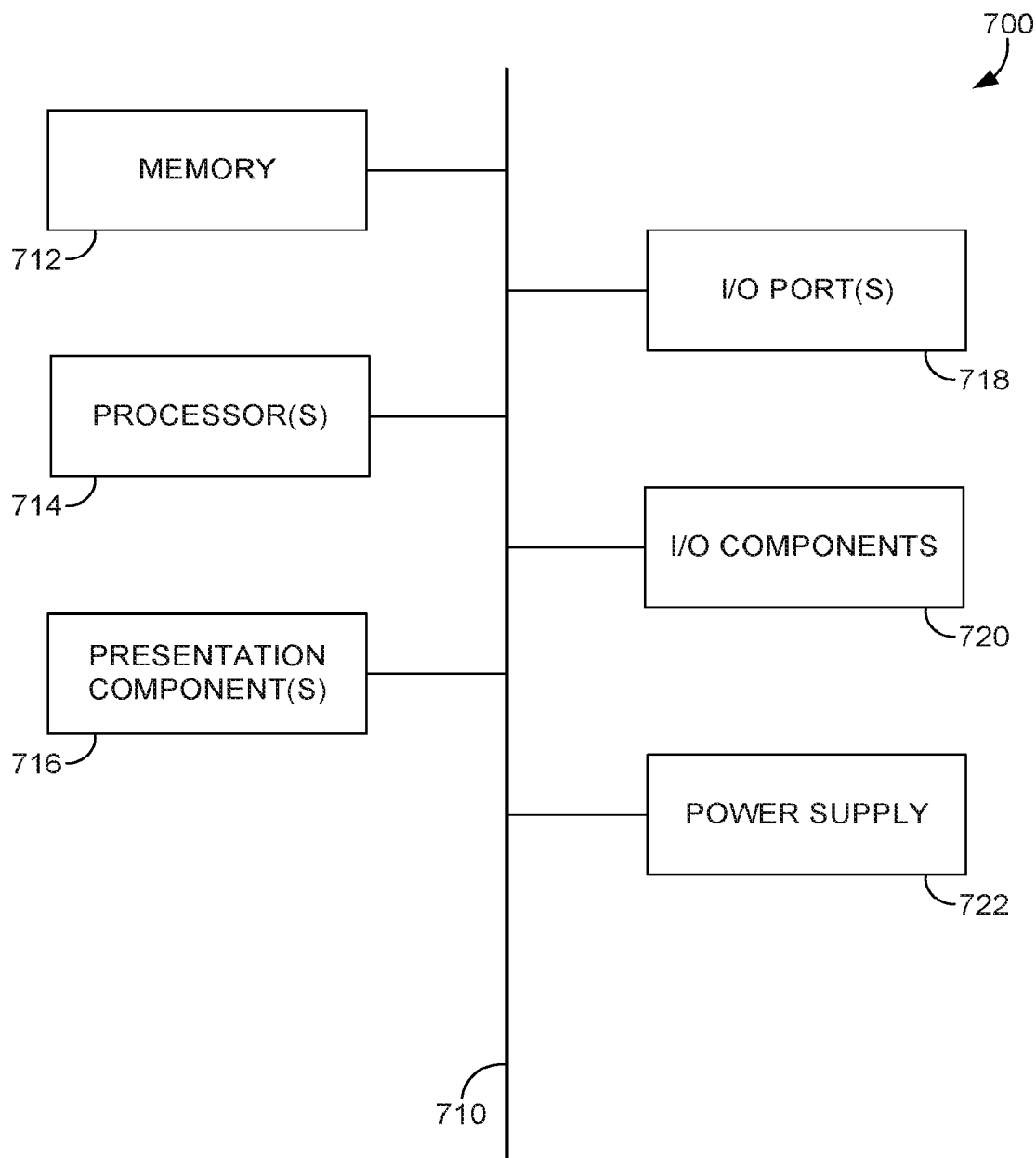
FIG. 7 is an example computing device suitable for use in practicing embodiments of the technology, in accordance with an aspect described herein.

Having described some aspects of the technology, example computing device 700 is provided in FIG. 7. Computing device 700 is one example of a suitable computing environment for practicing the technology, but is not intended to suggest any limitation as to the scope of use or functionality of the present technology. Neither should computing device 200 be interpreted as having any dependency or requirement relating to any one or combination of components illustrated.

In some cases, the technology may be described in the general context of computer code or machine-useable instructions, including computer-executable instructions such as program modules, being executed by a computer or other machine, such as a personal data assistant or other handheld device. Generally, program modules including routines, programs, objects, components, data structures, etc., refer to code that perform particular tasks or implement particular abstract data types. The technology may be practiced in a variety of system configurations, including handheld devices, consumer electronics, general-purpose computers, more specialty computing devices, etc. The technology may also be practiced in distributed computing environments where tasks are performed by remote-processing devices that are linked through a communications network.

With reference to FIG. 7, computing device 700 includes bus 710 that directly or indirectly couples the following devices: memory 712, one or more processors 714, one or more presentation components 716, input/output (I/O) ports 718, input/output components 720, and illustrative power supply 722. Bus 710 represents what may be one or more busses (such as an address bus, data bus, or combination thereof). Although the various blocks of FIG. 7 are shown with lines for the sake of clarity, in reality, delineating various components is not so clear, and metaphorically, the lines would more accurately be gray and fuzzy. For example, one may consider a presentation component such as a display device to be an I/O component. Also, processors have memory. The inventors recognize that such is the nature of the art, and reiterate that the diagram of FIG. 7 is merely illustrative of an exemplary computing device that can be used in connection with one or more embodiments of the present disclosure. Distinction is not made between such categories as "workstation," "server," "laptop," "hand-held device," etc., as all are contemplated within the scope of FIG. 7 and reference to "computing device," such as computing device 115 of FIG. 1.

With reference again to FIG. 7, computing device 700 typically includes a variety of computer-readable media. Computer-readable media can be any available media that can be accessed by computing device 700 and includes both volatile and nonvolatile media, removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 700. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 712 includes computer storage media in the form of volatile and/or nonvolatile memory. The memory may be removable, non-removable, or a combination thereof. Exemplary hardware devices include solid-state memory, hard drives, optical-disc drives, etc. Computing device 700 includes one or more processors that read data from various entities such as memory 712 or I/O components 720. Presentation component(s) 716 present data indications to a user or other device. Exemplary presentation components include a display device, speaker, printing component, vibrating component, etc.

I/O ports 718 allow computing device 700 to be logically coupled to other devices including I/O components 720, some of which may be built in. Illustrative components include a microphone, joystick, game pad, satellite dish, scanner, printer, wireless device, etc. The I/O components 720 may provide a natural user interface (NUI) that processes air gestures, voice, or other physiological inputs generated by a user. In some instance, inputs may be transmitted to an appropriate network element for further processing. A NUI may implement any combination of speech recognition, touch and stylus recognition, facial recognition, biometric recognition, gesture recognition both on screen and adjacent to the screen, air gestures, head and eye-tracking, and touch recognition associated with displays on the computing device 700. The computing device 700 may be equipped with depth cameras, such as, stereoscopic camera systems, infrared camera systems, RGB camera systems, and combinations of these for gesture detection and recognition. Additionally, the computing device 700 may be equipped with accelerometers or gyroscopes that enable detection of motion.

Figure 8:
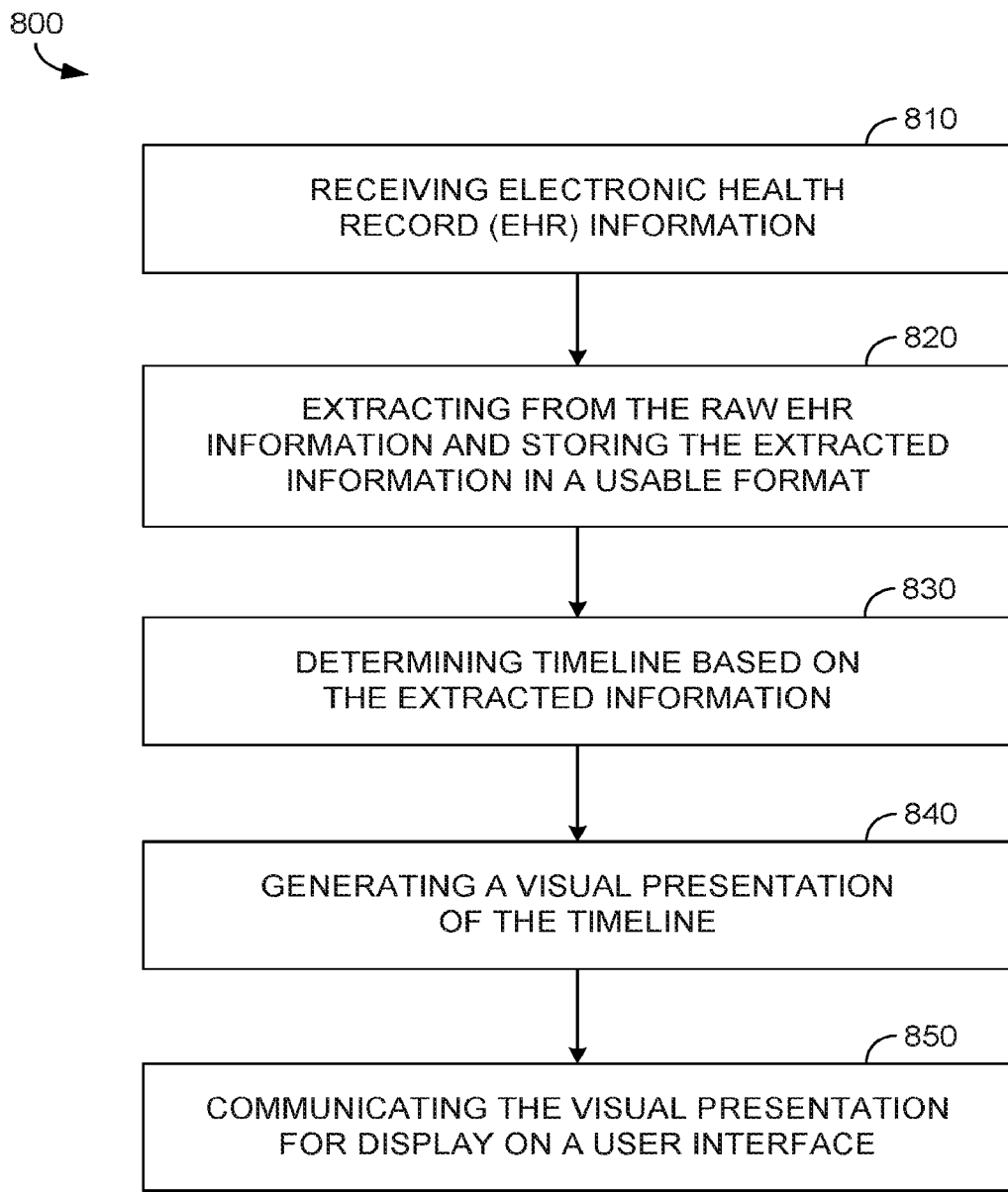
FIG. 8 is an example method for generating and visually communicating clinically relevant information, in accordance with an aspect described herein.

Turning now to FIG. 8, a method 800 of generating and visually communicating clinically relevant information in a manner that maintains context across various sized user interfaces is provided. In some aspects, the method may configure clinically relevant data to maintain trend context when displayed on a user interface. At block 810, EHR information about a patient is received. In some aspects, the EHR information may comprises a diagnostic event. For example, the EHR information may be received by receiver 122 from EHR system 102, from user interface 104, and/or from sensor 106. At block 820, patient information is extracted from the received raw EHR information. For example, extractor 124 may be used to extract patient information from the raw EHR information. The extracted information may be stored, such as in storage 108, in a usable format.

At block 830, a timeline is determined based on the extracted information. The timeline may be determined by timeline determiner 126. At block 840, a visual presentation of the timeline may be generated by GUI generator 128. The presentation may include a portion of the timeline represented as a timespan indication. The presentation may include a first and second timespan indication. In some aspects, the first and second timespan indications are mirrored and are scrollable to bring into view different portions of the timeline. In some aspects, the first timespan indication may be associated with a set of clinical diagnoses, while in some cases, the second timespan indication may be associated with a set of physiological parameters. In some cases, the presentation may include a medication area with a list of medications separated into groups based on classification. At block 850, the presentation may be communicated for display on a user interface.

Figure 9:
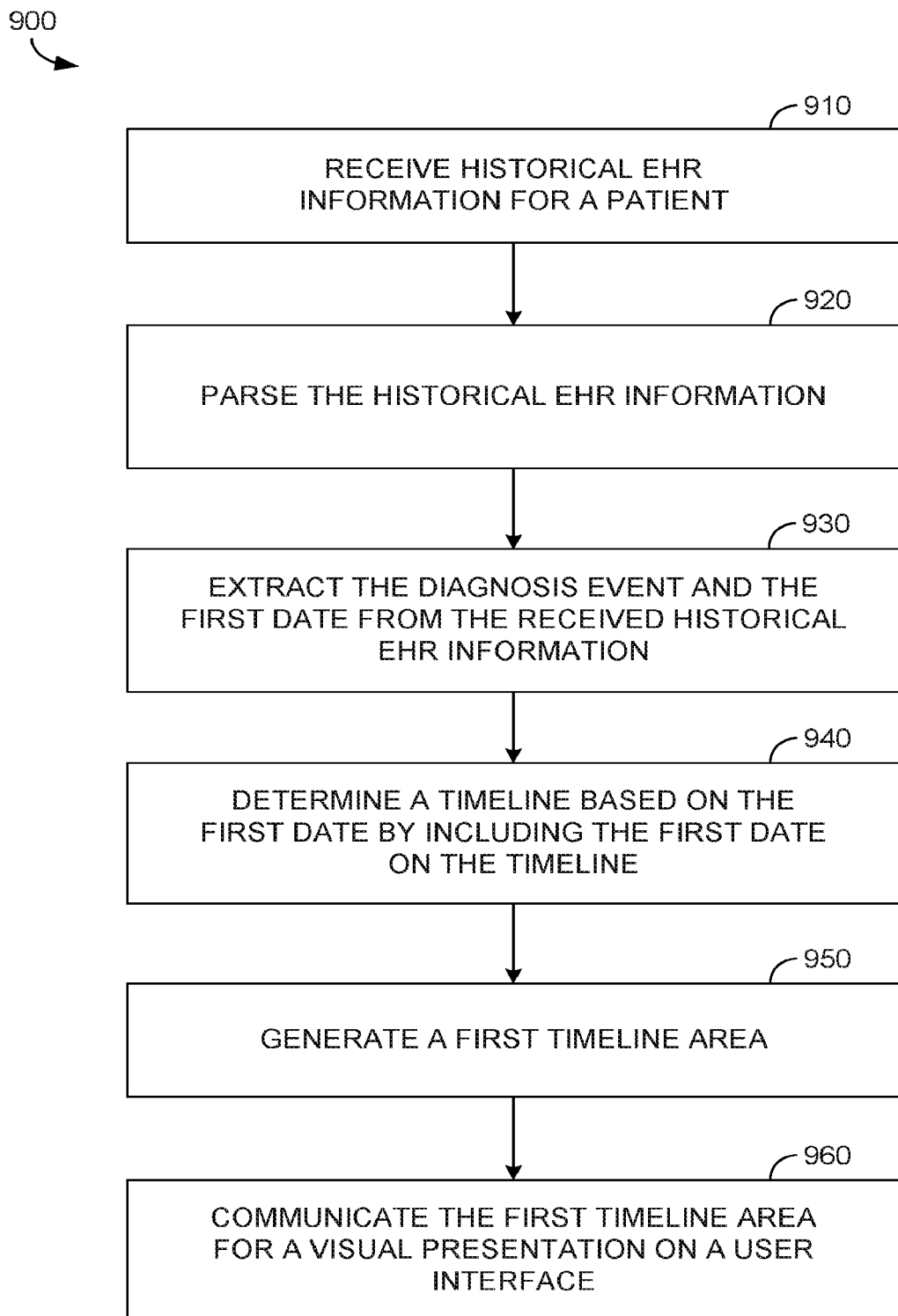
FIG. 9 is another example method for generating and visually communicating clinically relevant information, in accordance with an aspect described herein.

Turning now to FIG. 9, a method 900 for generating and visually communicating clinically relevant information in a manner that maintains context across various sized user interfaces is provided. At block 910, historical EHR information for a patient is received. In some cases, the EHR information may comprise a diagnostic event. At block 920, the historical EHR information may be parsed to determine a first date associated with the diagnosis event. At block 930, the diagnosis event and the first date are extracted from the received historical EHR information. At block 940, a timeline is determined based on the first date by including the first date on the timeline.

At block 950, a first timeline area is generated. In some cases, the first timeline area includes a vertical set of clinical diagnoses that includes a clinical diagnosis corresponding to the diagnosis event, a horizontal first indication of a timespan that includes at least a portion of the timeline with the first date, and a duration indicator horizontally aligned with the clinical diagnosis, the duration indicator having a first end vertically aligned with the first date and a duration region extending horizontally from the first end. At block 960, the first timeline area is communication for visual presentation on a user interface.

From the foregoing, it will be seen that this technology is one well adapted to attain all the ends and objects described above, including other advantages which are obvious or inherent to the structure. It will be understood that certain features and subcombinations are of utility and may be employed without reference to other features and subcombinations. This is contemplated by and is within the scope of the claims. Since many possible embodiments of the described technology may be made without departing from the scope, it is to be understood that all matter described herein or illustrated the accompanying drawings is to be interpreted as illustrative and not in a limiting sense.

What is claimed is:

1. A system for configuring clinically relevant data to maintain trend context when displayed on a user interface, the system comprising:
    at least one processor of a computing system;
    the user interface in communication with the at least one processor; and
    one or more computer-readable storage devices storing instructions that, when executed by the at least one processor, cause the at least one processor to:
    retrieve patient information for a patient from a plurality of data sources having different data formats, wherein the patient information includes diagnostic events and relevant dates associated with each diagnostic event;
    generate a user interface on a display screen;
    generate a first timeline area on the display screen in the user interface, wherein the first timeline area is generated to have a horizontal size based on at least a size of the display screen;
    generate a horizontal timespan presented horizontally between a first boundary and a second boundary within the first timeline area and including a set of non-linear dates;
    wherein the set of non-linear dates of the horizontal timespan is determined from at least a portion of the relevant dates corresponding to the diagnostic events from the patient information,
    the set of non-linear dates being provided in chronological order and spaced apart by an equal distance to form the non-linear timeline,
    display vertically, within the first timeline area, a set of clinical diagnoses based on the diagnostic events, and
    generate and display a duration indicator associated with a clinical diagnosis of the set of clinical diagnoses, the duration indicator having an onset date end associated with an onset date of the clinical diagnosis and a duration region beginning at the onset date end and extending horizontally therefrom to an end date determined from the relevant dates;

wherein the horizontal timespan includes a non-fixed area that is configured to be manipulated by a user input on the user interface; and in response to the user input, automatically expanding or compressing the horizontal timespan to change the set of non-linear dates that are displayed in the horizontal timespan that causes the associated duration regions of the duration indicators to expand or compress based on the set of non-linear dates that are displayed.

2. The system of claim 1, wherein the user interface further presents a second timeline area, the second timeline area comprising a second indication of the horizontal timespan presented horizontally and a set of diagnostic parameters presented vertically, wherein diagnostics results corresponding to the set of diagnostic parameters are presented in a grid relative to the second indication of the horizontal timespan and the set of diagnostic parameters.

3. The system of claim 2, wherein the user interface further presents a diagnostic result corresponding to a diagnostic parameter of the set of diagnostic parameters, the diagnostic result having an associated date included in the generated timeline.

4. The system of claim 1, wherein the duration indicator associated with the clinical diagnosis additionally has a termination date end associated with a termination date of the clinical diagnosis, the termination date end opposite the onset date end, and wherein the duration region extends horizontally from the onset date end to the termination date end.

5. The system of claim 1, wherein the horizontal timespan is configured to be manipulated by the user input by a scroll input, wherein the horizontal timespan is scrollable to change the set of non-linear dates which are maintained between the first boundary and the second boundary, and wherein scrolling the horizontal timespan changes a view of the generated timeline.

6. The system of claim 1, wherein the duration indicator comprises metadata links to an EHR, and wherein when an input is received at the duration indicator, the user interface further presents a pop-up window that includes additional information associated with the clinical diagnosis corresponding to the duration indicator.

7. The system of claim 1, wherein the user interface is configured to display a medication area, the medication area comprising a series of tabs, each tab associated with a medication classification, wherein the series of tabs is determined by one or more medications stored in an EHR, and wherein each tab toggles between a list of medications corresponding to the medication classification associated with the tab.

8. One or more computer-readable storage devices storing computer-executable instructions that, when executed a processor, cause the processor to at least perform functions comprising:

retrieve patient information for a patient from a plurality of data sources having different data formats, wherein the patient information includes diagnostic events and relevant dates associated with each diagnostic event;

generate a user interface on a display screen;

generate a first timeline area on the display screen in the user interface, wherein the first timeline area is generated to have a horizontal size based on at least a size of the display screen;

generate a horizontal timespan presented horizontally between a first boundary and a second boundary within the first timeline area and includes a set of non-linear dates;

wherein the set of non-linear dates of the horizontal timespan is determined from at least a portion of the relevant dates corresponding to the diagnostic events from the patient information, the set of non-linear dates being provided in chronological order and spaced apart by an equal distance to form the non-linear timeline, display vertically, within the first timeline area, a set of clinical diagnoses based on the diagnostic events, and generate and display a duration indicator associated with a clinical diagnosis of the set of clinical diagnoses, the duration indicator having an onset date end associated with an onset date of the clinical diagnosis and a duration region beginning at the onset date end and extending horizontally therefrom to an end date determined from the relevant dates;

wherein the horizontal timespan includes a non-fixed area that is configured to be manipulated by a user input on the user interface; and in response to the user input, automatically expanding or compressing the horizontal timespan to change the set of non-linear dates that are displayed in the horizontal timespan that causes the associated duration regions of the duration indicators to expand or compress based on the set of non-linear dates that are displayed.

9. The one or more storage devices of claim 8, wherein the computer-executable instructions are further configure to generate the user interface to display a second timeline, the second timeline comprising a second indication of the timespan presented horizontally and a set of diagnostic parameters presented vertically, wherein diagnostics results corresponding to the set of diagnostic parameters are presented in a grid relative to the second indication of the timespan and the set of diagnostic parameters.

10. The one or more storage devices of claim 9, wherein the computer-executable instructions are further configured to generate the user interface to display a diagnostic result corresponding to a diagnostic parameter of the set of diagnostic parameters, the diagnostic result having an associated date included in the generated timeline.

11. The one or more storage devices of claim 8, wherein the duration indicator associated with the clinical diagnosis additionally has a termination date end associated with a termination date of the clinical diagnosis, the termination date end opposite the onset date end, and wherein the duration region extends horizontally from the onset date end to the termination date end.

12. The one or more storage devices of claim 8, wherein the horizontal timespan is configured to be manipulated by the user input by a scroll input, wherein the horizontal timespan is scrollable to change the set of non-linear dates which are maintained between the first boundary and the second boundary, and wherein scrolling the horizontal timespan changes a view of the generated timeline.

13. The one or more storage devices of claim 8, wherein the duration indicator comprises metadata links to an EHR, and wherein when an input is received at the duration indicator, the user interface further presents a pop-up window that includes additional information associated with the clinical diagnosis corresponding to the duration indicator.

14. The one or more storage devices of claim 8, wherein the user interface is configured to display a medication area, the medication area comprising a series of tabs, each tab associated with a medication classification, wherein the series of tabs is determined by one or more medications stored in an EHR, and wherein each tab toggles between a list of medications corresponding to the medication classification associated with the tab.

15. A method performed by a computing system, the method comprising:

retrieving patient information for a patient from a plurality of data sources having different data formats, wherein the patient information includes diagnostic events and relevant dates associated with each diagnostic event;

generating a user interface on a display screen;

generating a first timeline area on the display screen in the user interface, wherein the first timeline area is generated to have a horizontal size based on at least a size of the display screen;

generating (i) a horizontal timespan presented horizontally within the first timeline area and including a set of non-linear dates, (ii) a set of clinical diagnoses based on the diagnostic events and being presented vertically, and (iii) a duration indicator associated with a clinical diagnosis of the set of clinical diagnoses;

wherein the set of non-linear dates of the horizontal timespan is determined from at least a portion of the relevant dates corresponding to the diagnostic events from the patient information;

wherein the set of non-linear dates being provided in chronological order and spaced apart by an equal distance to form the non-linear timeline;

wherein the duration indicator is generated having an onset date end associated with an onset date of the clinical diagnosis and a duration region beginning at the onset date end and extending horizontally therefrom to an end date determined from the relevant dates;

wherein the horizontal timespan includes a non-fixed area that is configured to be manipulated by a user input on the user interface; and in response to the user input, automatically expanding or compressing the horizontal timespan to change the set of non-linear dates that are displayed in the horizontal timespan that causes the associated duration regions of the duration indicators to expand or compress based on the set of non-linear dates that are displayed.

16. The method of claim 15, wherein the duration indicator associated with the clinical diagnosis additionally has a termination date end associated with a termination date of the clinical diagnosis, the termination date end opposite the onset date end, and wherein the duration region extends horizontally from the onset date end to the termination date end.

17. The method of claim 16, scrolling the horizontal timespan between a first boundary and a second boundary in response to the user input to expand or compress the horizontal timespan, and wherein scrolling the horizontal timespan changes a view of the non-linear timeline.

18. The method of claim 15, wherein the duration indicator comprises metadata links to an EHR, and wherein when an input is received at the duration indicator, the user interface further presents a pop-up window that includes additional information associated with the clinical diagnosis corresponding to the duration indicator.

19. The method of claim 15, wherein a date included in the horizontal timespan comprises metadata links to an EHR, and wherein when an input is received at the date, the user interface further presents a pop-up window that includes additional information associated with the date.

20. The method of claim 15, further comprising generating and displaying a medication area within the user interface, the medication area comprising a series of tabs, each tab associated with a medication classification, wherein the series of tabs is determined by one or more medications stored in an EHR, and wherein each tab toggles between a list of medications corresponding to the medication classification associated with the tab.

\* \* \* \* \*